United States Patent
Takahashi et al.

(10) Patent No.: US 7,171,249 B2
(45) Date of Patent: Jan. 30, 2007

(54) MEDICAL DEVICE

(75) Inventors: Masahiro Takahashi, Haibara-Gun (JP); Kazumi Yokoyama, Haibara-Gun (JP)

(73) Assignee: Nikkiso Co., Ltd., Tokyo (JP)

( * ) Notice: Subject to any disclaimer, the term of this patent is extended or adjusted under 35 U.S.C. 154(b) by 549 days.

(21) Appl. No.: 10/414,448

(22) Filed: Apr. 15, 2003

(65) Prior Publication Data

US 2003/0212314 A1    Nov. 13, 2003

(30) Foreign Application Priority Data

Apr. 15, 2002 (JP) ............................. 2002-112471
Feb. 25, 2003 (JP) ............................. 2003-047469

(51) Int. Cl.
*A61B 5/00* (2006.01)
*A61M 37/00* (2006.01)
*G09G 5/00* (2006.01)
*C02F 1/00* (2006.01)
*B01D 11/00* (2006.01)

(52) U.S. Cl. ................... 600/310; 604/5.01; 604/6.01; 128/920; 345/625; 210/739; 210/645

(58) Field of Classification Search ............... 604/4.01, 604/6.1, 5.01–5.04, 6.01–6.07, 6.09, 6.11, 604/6.13–6.16; 422/44–48; 600/300, 301; 710/1, 5–7; 128/905, 920, 922–925; 345/418, 345/589, 511, 619, 625, 629, 689, 440, 441, 345/467, 473, 474, 156, 168–169, 171–173, 345/184, 501, 520, 522, 1.1, 1.2, 3.1, 905; 700/1, 9, 10, 28, 86–89, 78–84, 90, 17, 18, 700/21, 26, 27; 704/231, 235, 236, 240; 714/1, 2, 25, 48, 49, 57, 100

See application file for complete search history.

(56) References Cited

U.S. PATENT DOCUMENTS

| | | | | |
|---|---|---|---|---|
| 5,056,059 | A | * | 10/1991 | Tivig et al. .................. 715/828 |
| 5,609,770 | A | * | 3/1997 | Zimmerman et al. ........ 210/739 |
| 5,653,887 | A | * | 8/1997 | Wahl et al. .................. 210/745 |
| 5,788,851 | A | * | 8/1998 | Kenley et al. ............... 210/739 |
| 5,956,023 | A | * | 9/1999 | Lyle et al. ................... 715/771 |

* cited by examiner

*Primary Examiner*—Patricia Bianco
(74) *Attorney, Agent, or Firm*—Darby & Darby PC (57) ABSTRACT

A medical device having an operation input unit for an operator to enter instructions and a operation unit for performing prescribed operations required for medical treatment based on input from said operation input unit, including a dialysis device that purifies patient's blood by means of extracorporeal circulation. Further having a human body detection unit for detecting the operator's presence in the vicinity of operation input unit, and a control unit that provides control for allowing input operation unit to instruct the operation unit's operations, or allowing the operation unit to operate based on the input entered into operation input unit, only when said human body detection unit is detecting the operator.

16 Claims, 5 Drawing Sheets

MEDICAL DEVICE

BACKGROUND OF THE INVENTION

1. Field of the Invention

The invention relates to a blood purifying device for purifying the patient's blood by means of extracorporeal circulation or an infusion device for administering drugs into the patient's body.

2. Description of Related Art

In a conventional dialysis treatment, a puncture needle attached to the distal end of the blood circuit is caused to puncture into the patient's body, while the patient's blood is caused to make an extracorporeal circulation in order to purify the blood by means of a dialyzer connected to the circuit. Such a dialyzer is connected to a dialysis device, wherein said dialysis device provides a dialysate and discharges the dialysate containing waste products of the blood.

In other words, a blood passage (the ends of which are connected to the arterial side blood circuit and the venous side blood circuit respectively), through which the patient's blood flows, and a dialysate passage (the ends of which are connected to the dialysate induction line and the dialysate discharge line respectively), through which the dialysate flows, are formed in the dialyzer, and these passages are separated by a hollow thread membrane, so that it is possible to diffuse the products contained in the blood flowing through the blood passage across the membrane into the dialysate, thus purifying the blood, and return the purified blood back to the patient's body.

The dialysis device is provided, primarily inside the device, with an operating input unit for the operator, such as a medical doctor, to start or stop the dialysis treatment, or to set up or change the dialysis treatment condition, as well as a operation unit that executes prescribed operations (including the start and stop of the device and controls based on various setups) based on input signals entered through said input unit. The operation input unit contains touch operating type switches displayed on the liquid crystal display panel, operating switches and operating dials that can be operated for entering input data mechanically, etc.

There is a possibility, for example, that the terminal point of an operating switch can be held in a contacting state temporarily or continuously due to a malfunction of said operation input unit or an external noise, while the operator is not operating. Such a problem must be avoided as it can threaten the patient's life in a medical device such as a dialysis device.

In order to avoid the operation unit from functioning due to a temporary contact of the terminal point of an operating switch although the operator is not operating, a medical device has been proposed wherein a switch is not recognized to be pressed unless said switch is continued to be pressed for a prescribed period of time (hereinafter called "maintained operation"). Also, another medical device has been proposed wherein a timer is provided for detecting the same operating condition is held continuously over a prescribed period of time and determines that a malfunction has occurred when said timer detects such an incidence in order to avoid the operation unit from operating when the same operating condition continues over a prescribed (long) period of time although the operator is not operating. Those medical devices improve the safety during treatments as they prevent the operation unit from causing unintended operations due to malfunctions or external noises. These prior arts are not related to any publicized inventions, so that there is no prior art documents to be referred here.

Problems to be Solved by the Invention

However, those medical devices of the prior art needing maintained operations accept operating input only when a switch is pressed continuously for a prescribed time, it presented a problem that it is difficult to achieve the ease of operation and safety of the device simultaneously. In other words, it tends to cause misrecognition of an error signal as a normal signal if the prescription time for a maintained operation is set too short, while it may reduce the ease of operation as it requires to be pressed too long if said prescription time is set too long.

Moreover, in case of a medical device of the prior art equipped with a timer, it may deteriorate the ease of operation as it tends to cause normal operation input by the operator as a malfunction if the set time for recognizing malfunctions is chosen too short, while safety may be jeopardized in the operation of the operation unit as it takes too long to recognize malfunctions if the set time is chosen too long, thus making it extremely difficult to properly set the time for avoiding malfunctions.

The invention was made under such a circumstance, and provides a medical device which makes it possible to achieve both the ease of operation at the operation input unit and the patient's safety at the same time.

SUMMARY OF THE INVENTION

The invention is a medical device including an operation input unit for an operator to enter instructions and a operation unit for performing prescribed operations required for medical treatment based on input from said operation input unit, characterized by further having a human body detection means for detecting the operator's presence in the vicinity of said operation input unit, and a control unit that provides control function for allowing the input operation unit to instruct the operation unit's operations, or allowing the operation unit to operate based on the input entered into the operation input unit, only when said human body detection means is detecting the operator.

Another embodiment of the invention is a medical device wherein said control function provided by said control unit can be cancelled.

Further, embodiments can include a medical device having a display means for displaying specific information such as operation status of said operation unit, wherein said display means executes a specific display when said human body detection means detects an operator. Also the display means can include a liquid crystal display panel equipped with a backlight, and executes the specific display by lighting said backlight or raising its intensity when said human body detection means detects an operator.

Another embodiment includes a sound output means for issuing specific sounds in accordance with operation conditions of said operation unit, and the output by said sound output means is controlled based on the detection of the presence of an operator by said human body detection means.

An embodiment can include an external indicator light that illuminates in accordance with operation conditions of said operation unit, wherein the luminescence intensity of said external indicator light is made controllable based on the detection of an operator by said human body detection means.

An embodiment of the human body detection means can include an illumination means for irradiating an infrared light and a light receiving means for receiving its reflection, and the presence of an operator in the vicinity of said operation input unit is detected as said light receiving means receives the reflection.

DETAILED DESCRIPTION OF THE PREFERRED EMBODIMENTS

Figure 1:
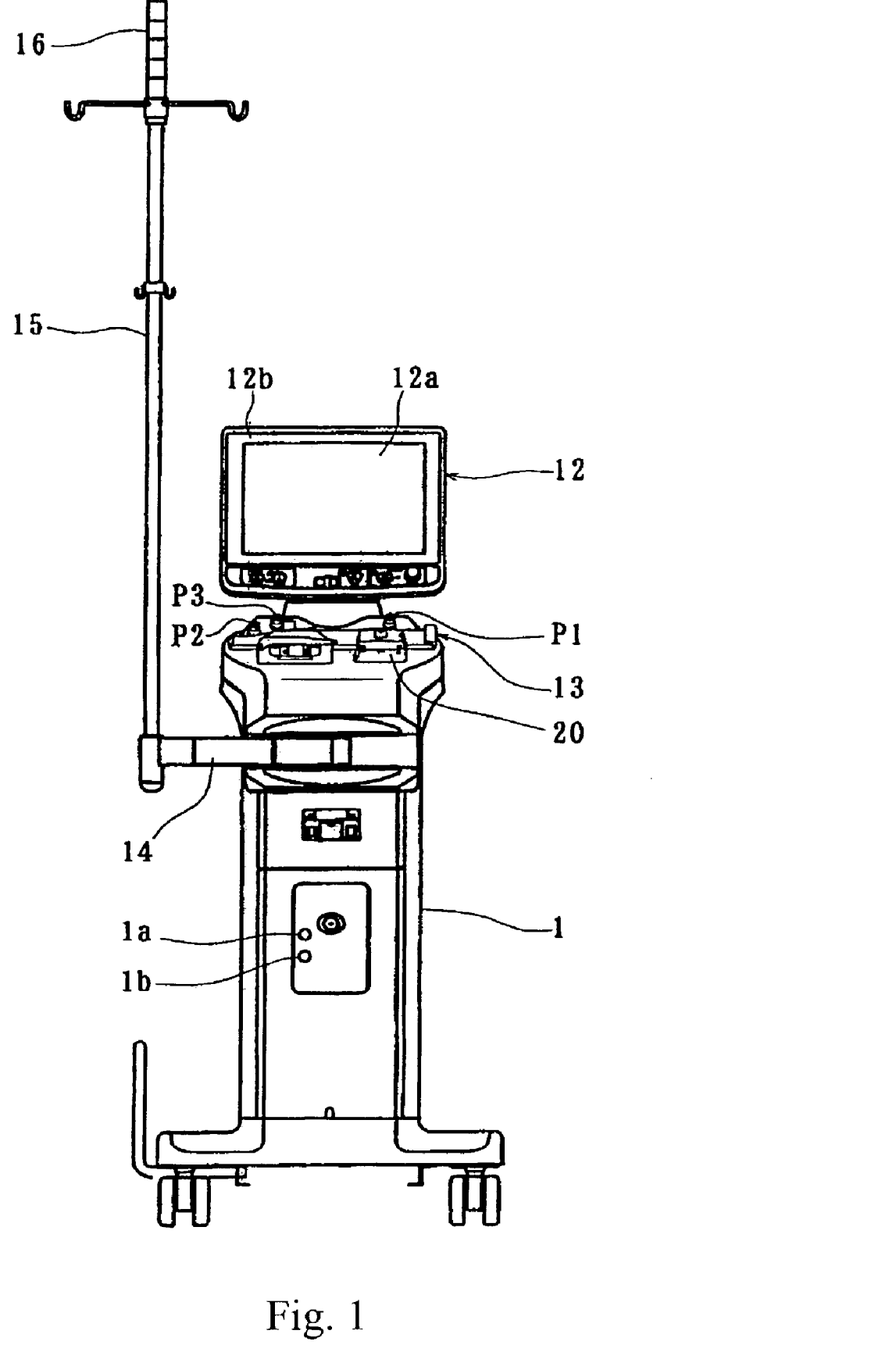
FIG. 1 is a front view of a dialysis device according to an embodiment of the present invention.

A preferred embodiment of the invention will be described below referring to the accompanying drawings. The medical device according to this embodiment comprises a dialysis device that circulates the patient's blood extracorporeally through a blood circuit, supplies a dialysate to a dialyzer (blood purifier) connected to said blood circuit, and collects the dialysate containing waste products found in the blood as it is discharged from the dialyzer, and consists primarily of a dialysis device main body 1 and an operation input unit 12 as shown in FIG. 1.

Figure 2:
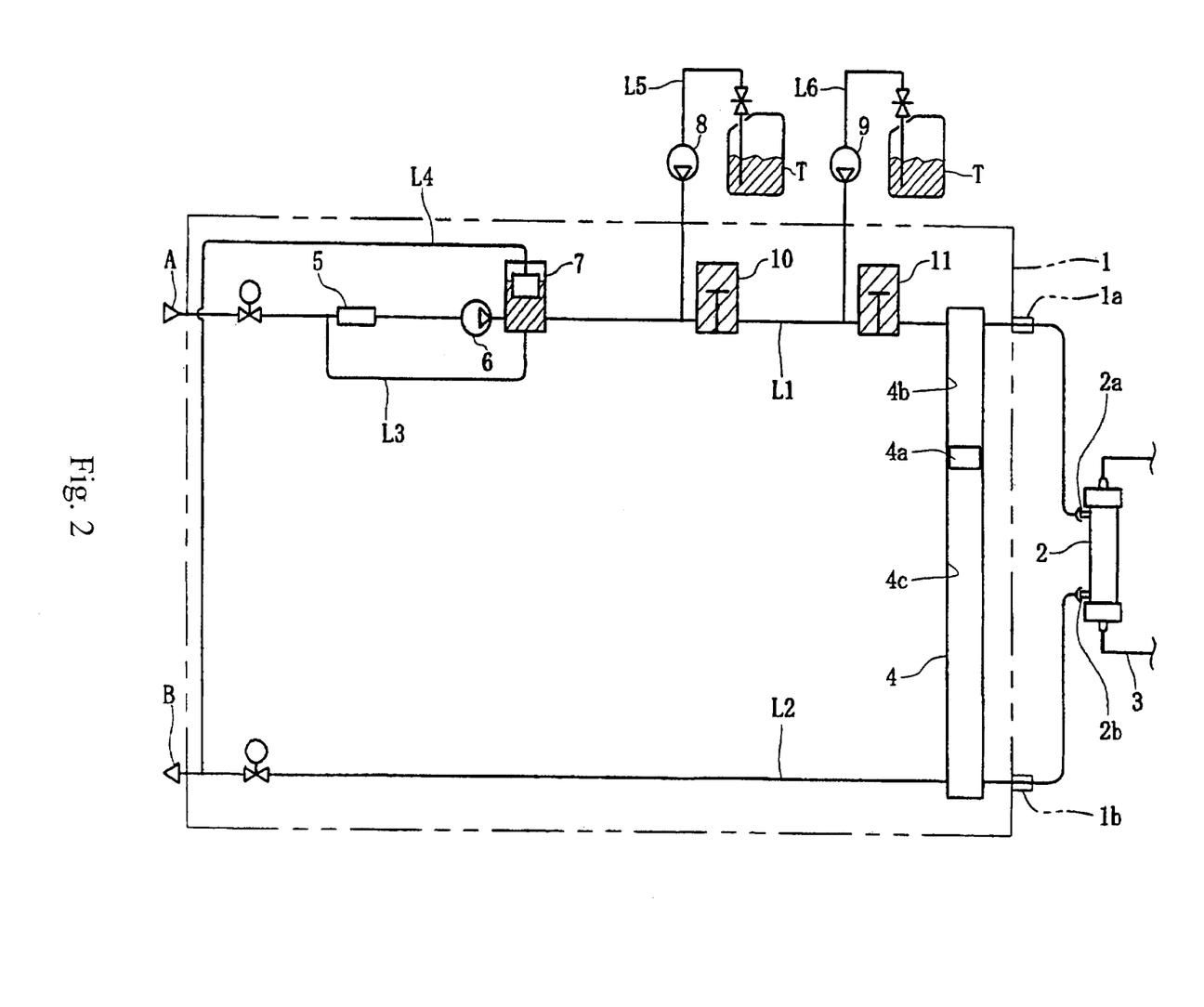
FIG. 2 is a view showing a frame format of the inside of the main body of the dialysis device according to the embodiment of the present invention.

Dialysis device main body 1 have two ports (a supply port 1a for supplying the dialysate into the dialyzer, and an induction port 1b for inducing the dialysate discharged from the dialyzer) to be connected to the dialyzer formed on its front, and these supply port 1a and induction port 1b are connected to dialysate induction port 2a and dialysate discharge port 2b connected to a blood circuit 3 respectively as shown in FIG. 2.

A supply line L1 connecting a port A connected to a washing water supply source with supply port 1a as well as a discharge line L2 connecting a port B for discharging the dialysate after dialysis with induction port 1b are provided inside dialysis device main body 1, and a reciprocating pump 4 is provided across these supply line L1 and discharge line L2. Reciprocating pump 4 is provided with a plunger 4a that reciprocates separating the internal pump chamber into two sections, a pump chamber 4b that communicates with supply line L1 and a pump chamber 4c. A reverse flow check mechanism for reciprocating pump 4 is not shown.

Supply line L1 is provided with a deaeration mechanism comprising a heater 5, a deaeration pump 6, a deaeration chamber 7, a circulation line L3 and an air discharge line L4 in order to make it possible to remove air contained in the washing water supplied by port A, and also with a mixing mechanism comprising tank lines L5 and L6 connected with a tank T containing the stock solution of the dialysate, suction pumps 8 and 9 connected to tank lines L5 and L6, and mixing chambers 10 and 11, thus making it possible to prepare a dialysate with a specified concentration. Although it is not shown in the diagram, an ultra filtration pump and others are provided on the discharge line L2 side of reciprocating pump 4.

The operation unit of the invention consists of various devices formed on said dialysis device main body 1, and performs certain operations on the patient's body based on input signals from operation input unit 12. In other words, the discharge volume control of a pump, opening and closing of a solenoid valve and others are primarily executed based on the input information from operation input unit 12 constituting the treatment conditions set up by the operator such as a medical doctor, and are the so-called operations provided by the operation unit.

Furthermore, formed on top of dialysis device main body 1, are a syringe pump 13 (drug infusion pump) for administering a drug into blood circuit 3, an air bubble detector 20 for detecting bubbles in the blood flowing through the venous side blood circuit of blood circuit 3, and connection ports P1 through P3 of the detection line for detecting the blood circuit pressure by being connected to a drip chamber (not shown) of said blood circuit 3. An arm 14 is formed on the side of dialysis device main body 1 and a pole 15 is extending upward from said arm 14. At the distal end of said pole 15 formed is an external indicator light 16 that consists of LED and lights in accordance with operation conditions of the operation unit.

Lighting of external indicator light 16 makes it possible to notify medical staff including doctors who are located far away about the operating conditions (in process of dialysis, completion of dialysis, abnormality, etc.) of the dialysis device, thus saving their troubles in checking the status. The luminance (lightness) of such an external indicator light 16 is adjustable and is turned on and off based on the signal from a control unit 19 (FIG. 3) to be described later.

Operation input unit 12 is provided for the operator such as a medical doctor or a nurse to give instructions to the operation unit on dialysis device main body 1, and mainly consists of a liquid crystal display panel 12a (display unit) for displaying operating conditions of the operation unit, and its cabinet 12b. A backlight (not shown) is built into liquid crystal panel 12a, and when a human body detection means 18, which is to be described later, detects an operator, it gets turned on or its light intensity is increased to make the prescribed display more visible.

Figure 4:
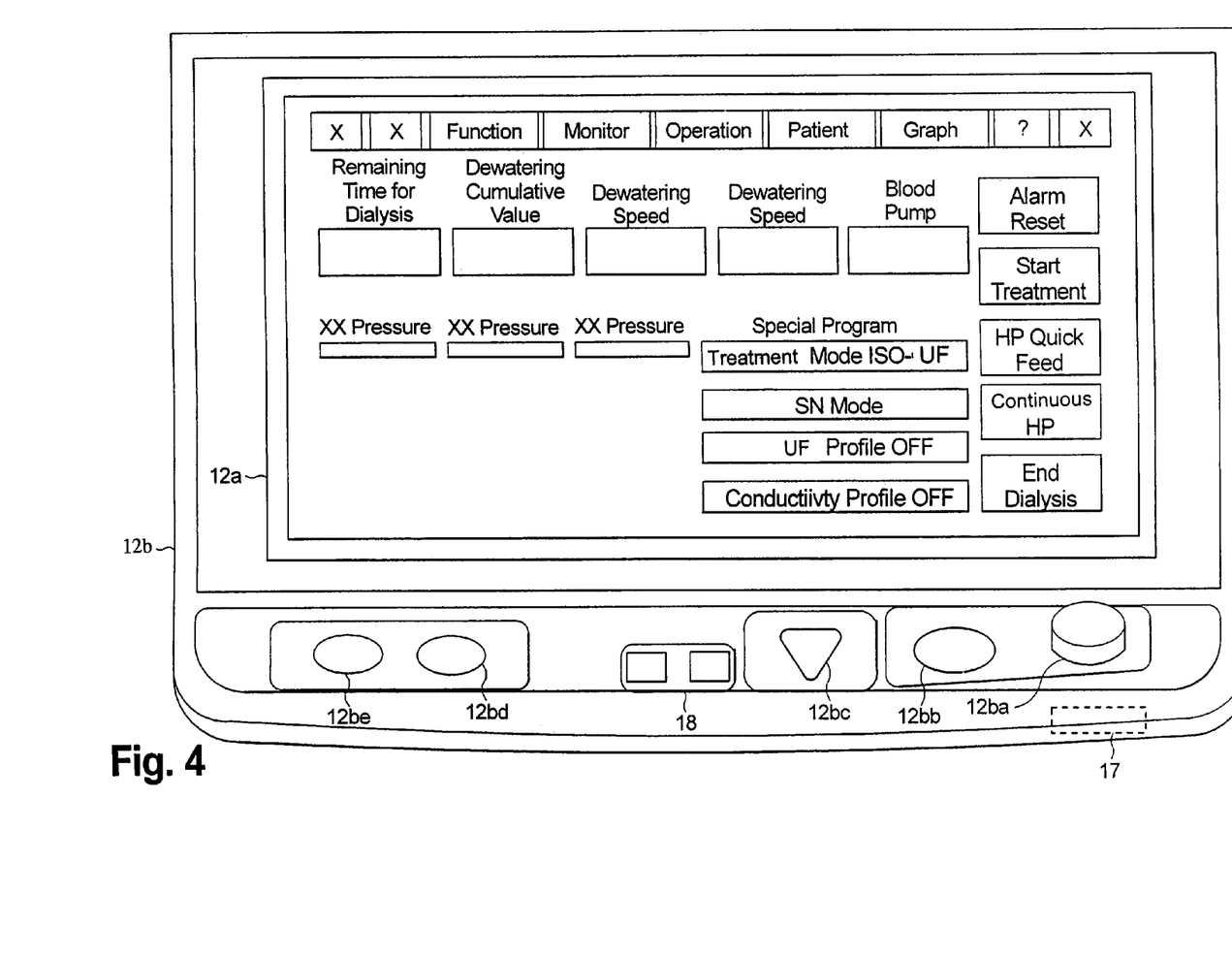
FIG. 4 is an enlarged front view of the operation input unit of the dialysis device according to the embodiment of the present invention.

As shown in FIG. 4, in addition to displaying various operating statuses (including the setup status) of the operation unit such as the dialysis remaining time and the water removal speed, liquid crystal display panel 12a displays touch-operation type switches that can be operated by finger-touching specific areas of the screen (for example, rectangular areas provided on the right side of the screen with notations such as "Alarm Reset," "Start Treatment," "HP Quick Feed," "Continuous HP," and "End Dialysis," as well as rectangular areas provided in the middle of the screen with notations such as "Treatment Mode," "SN Mode," "Water Removal Profile," and "Conductance Profile").

In addition to the operation input unit comprising the abovementioned touch-operation type switches, operating dial 12ba and a plurality of operating buttons 12bb through 12be are provided on the bottom part of cabinet 12b or display panel 12a so that specific instructions for the operation unit can be entered by means of these operating dial 12ba and operating buttons 12bb through 12be. All of these are integrally called the operation input unit.

A speaker 17 is provided inside cabinet 12b as a sound output means for generating specific sounds such as alarm sound depending on the operating status of the operation unit. The sound volume of said speaker 17 is adjustable and is turned on based on the signal from a control unit 19 (FIG. 3) to be described later. A plurality of openings are provided on the wall of cabinet 12b that faces the output part of said speaker 17 in order to cause the sound to be emitted efficiently to the outside.

Figure 5:
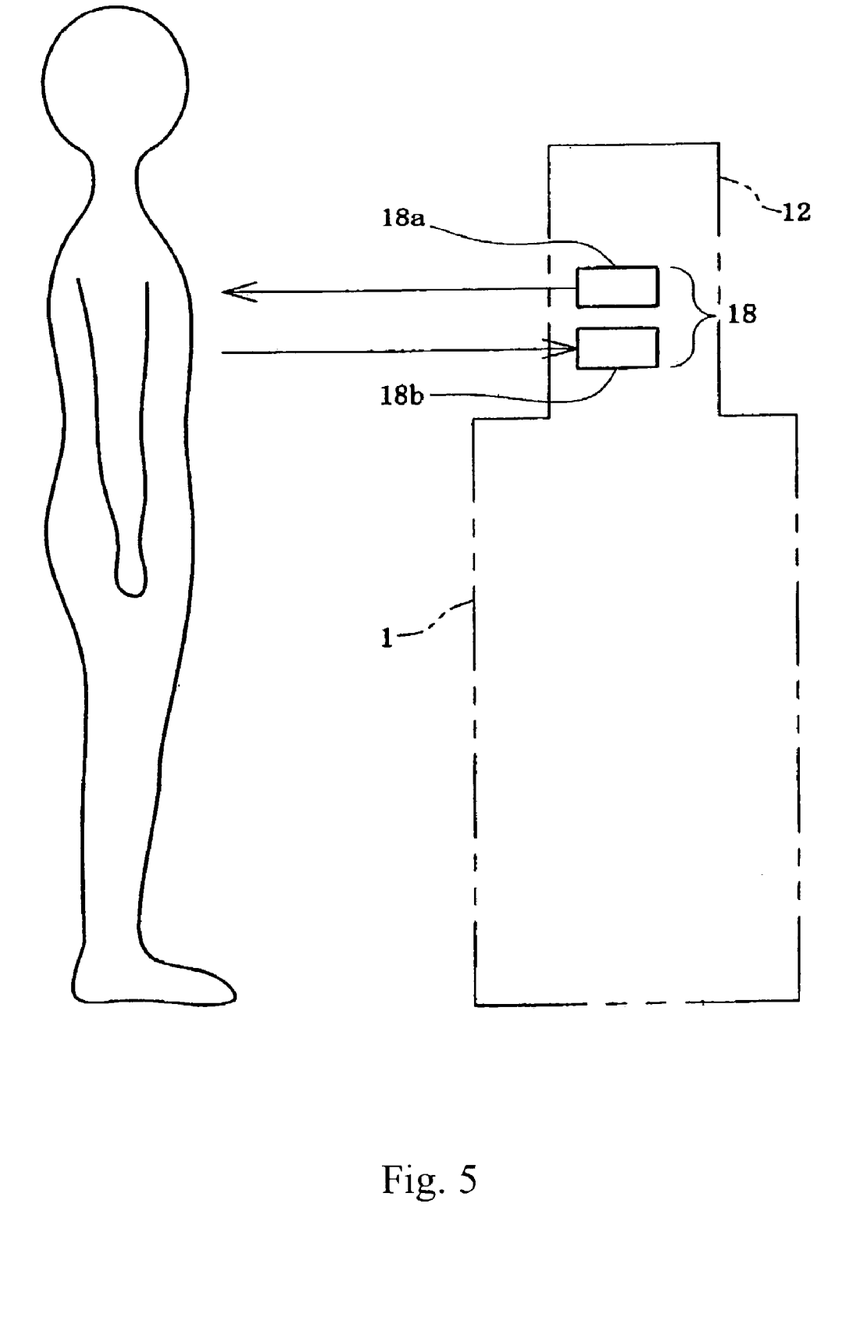
FIG. 5 is a view showing a frame format for describing the operation of the human body detection means of the dialysis device according to the embodiment of the present invention.

A human body detection means 18 is provided at the bottom part of cabinet 12b for detecting the presence of the operator in the vicinity of operation input unit 12. Human body detection means 18 comprises, as shown in FIG. 5, an light irradiating means 18a for irradiating infrared light in the forward direction and a reflection infrared sensor equipped with a light receiving means 18b for receiving the reflection wave in order to detect the presence of the operator in the forward vicinity of operation input unit 12 as light receiving means 18b receives the reflection.

When the operator is in the forward vicinity of operation input unit 12, infrared rays irradiated forward of operation input unit 12 by light irradiating means 18a bounce off the operator so that they are received by light receiving means 18b, thus causing it to detect the presence of the operator, while the infrared rays irradiated by light irradiating means 18a do not bounce off the operator if the operator is not in the forward vicinity of operation input unit 12 so that they are not received by light receiving means 18b, thus causing it to recognize that the operator is not in the vicinity.

Hence, the presence of the operator can be always accurately detected by irradiating and receiving infrared rays. Since the infrared rays are constituted in such a way as to be irradiated only forward of operation input unit 12, it is not affected by the patient being treated by dialysis on the side, so that it detects only the operator and prevents any misdetection. It is also possible to use other means that can detect the presence of the operator in the vicinity of operation input unit 12 (e.g., a sensor that detects the heat a human body emits, or image recognition means that detects the operator based on an image of the vicinity of operation input unit 12, etc.) in place of such a human body detection means constituted as described above.

Figure 3:
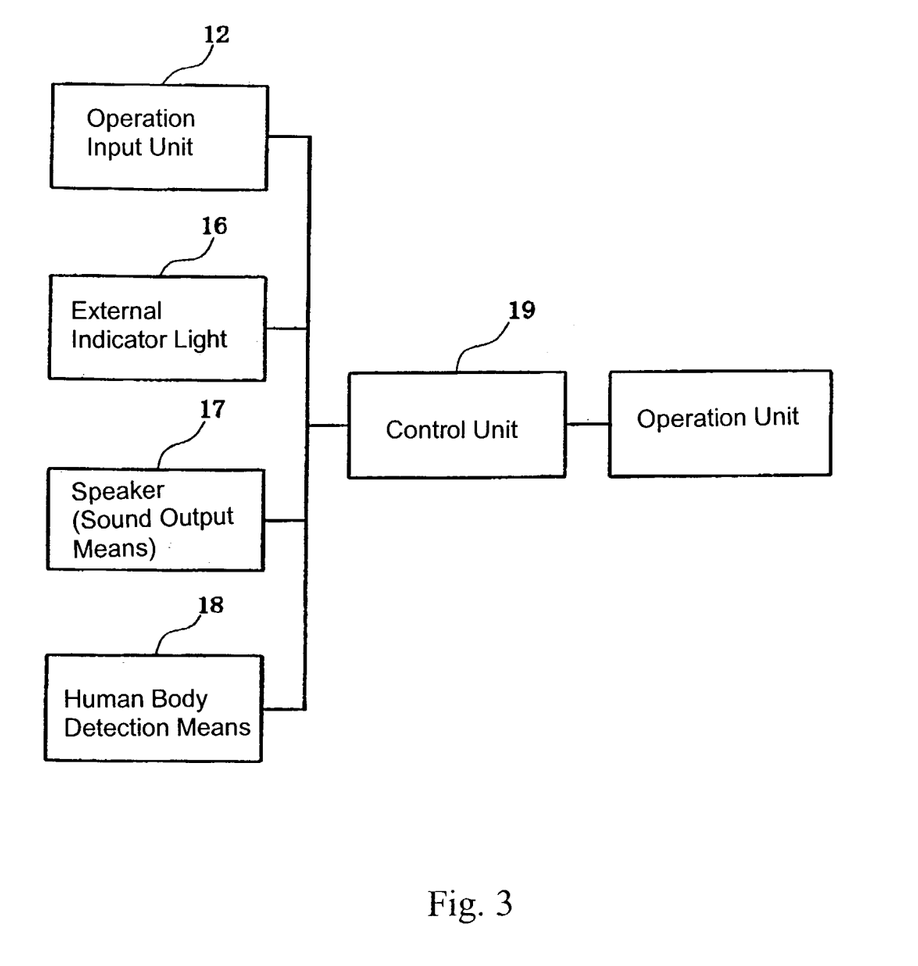
FIG. 3 is a block diagram showing the control unit of the dialysis device according to the embodiment of the present invention and peripheral equipment electrically connected thereto.

On the other hand, a control unit 19 that comprises an arithmetic means such as a microcomputer is provided inside dialysis device main unit 1 as shown in FIG. 3, and said control unit 19 is electrically connected electrically with operation input unit 12, external indicator light 16, speaker 17, and human body detection means 18 as well as to the operating unit. Control unit 19 is constituted in such a way to allow the operation unit to perform its operations based on the input from the operation input unit only when human body detection means 18 is detecting the operator.

When human body detection means 18 detects the operator, it transmits a detection signal to control unit 19, control unit 19 recognizes the presence of the operator, accepts an input signal when it receives the operation signal for the operation unit 12 while the detection signal is being received, but rejects an input signal received from operation input unit 12 while the detection signal is not being received, judging that it is not an input by the operator, and issues no operation instruction to the operation unit based on said input signal Therefore, control unit 19 accepts the operation input and the operation unit executes operations based on input from operation input unit 12 only when human body detection means 18 is detecting the operator, so that operations due to malfunction when the operator is not present in the vicinity of operation input unit 12 are prevented, thus providing both the ease of operation at operation input unit 12 and the patient's safety simultaneously.

For example, in case when an air bubble detector 20 (see FIG. 1) is used as an operation unit of the invention, there is a possibility of malfunction when air bubble detector 20 turns off during the treatment due to a malfunction of operation input unit 12. According to this embodiment, there is no way air bubble 20 gets turned off without the operator being detected and no input is accepted when the operator is not in the vicinity of operation input unit 12, so that a problem mentioned above can be avoided.

Moreover, if the quick feed switch of syringe pump 13 (see FIG. 1) (drug infusion pump) is stuck in the ON position due to a malfunction of operation input unit 12 while there is nobody in the vicinity of operation input unit 12, it can cause as excessive infusion of the drug, but this embodiment prevents such an input operation when there is nobody in the vicinity of operation input unit 12 so that such an erroneous operation cannot occur.

Although it is controlled in this embodiment to allow operation input by operation input unit 12 only when the operator is detected by human body detection means 18, it can be controlled additionally to allow the operation unit to operate only when the operator is detected by human body detection means 18. In other words, it is possible to constitute in such a way that, if operation input is executed by operation input unit 12 while no detection is made by human body detection means 18, the input by operation input unit 12 may be allowed but no operation based on the input is allowed.

It is also possible to constitute in such a way as to increase the safety when the operator is not present by reducing the control quantity compared to the control quantity of the operation unit when the operator is detected by human body detection means 18.

Moreover, it can be constituted in such a way that, in case the operation unit is supposed to operate after a prescribed time period according to an operating condition entered through operation input unit 12, said operation condition input is accepted only when the operator is in the vicinity of the dialysis device, but the operation unit's operation based on said input information can be executed without having to have a doctor, etc. This prevents not only erroneous input operation, but also allows a smooth treatment as the operation can be performed based on the preset condition without having to have a doctor, etc.

The abovementioned control by means of control unit 19 can be cancelled by other operating means (e.g., mechanical switches provided on cabinet 12b). This enables the operator to choose either to allow operations of the operation unit based on input information through operation input unit 12 only when the operator is detected by human body detection means 18, or to allow operations of the operation unit based on input information through operation input unit 12 regardless of whether the operator is detected by human body detection means 18 or not, thus improving the ease of operation on the dialysis device.

As mentioned before, it is controlled in such a way that the backlight of liquid crystal display panel 12a is turned on or the intensity of the light is increased when human body detection means 18 detects the operator and transmits the detection signal to control unit 19. By turning on the light, the display of liquid crystal display panel 12a becomes more visible and makes it possible to perform input operation by means of the aforementioned touch operation type switches. Consequently, as the display and input operation by means of liquid crystal display panel 12a having the dual functions of display means and operation input means are enabled only when the operator is detected by human body detection means 18, it is not only possible to achieve ease of operation and safety simultaneously, but also to minimize the power consumption of the display means, thus reducing the running cost of the medical device.

Moreover, in contrast to the prior art in which the operator such as a medical doctor had to turn on or increase the intensity of the backlight each time when they want to check the data displayed on liquid crystal display panel 12a, which they need to do regularly during a dialysis treatment, the abovementioned constitution of the present invention turns on or increases the intensity of the backlight automatically when the operator such as a medical doctor walks up to the front of operation input unit 12, making it a labor saving device.

It is also controlled in such a way as to turn off the output sound of speaker 17 when the detection signal is transmitted to control unit 19. In a case of a device wherein speaker 17 emits a warning sound when an abnormality occurs or a dialysis treatment is finished, this makes it possible for the operator such as a medical doctor to turn off the sound by simply walking up to the front of operation input unit 12, making it labor saving compared to a case where the sound has to be turned off by a manual operation. The output sound can be controlled not only by turning it off completely but also by reducing the output volume when the detection signal is received by control unit 19. This way the effect of the sound to the environment can be minimized.

It is also controlled to reduce the light 16 intensity of external indicator light 16 when control unit 19 receive the detection signal. This makes it possible to recognize various operating statuses of the operation unit or the operator's operation from a far off place while minimizing the effect of the lighting of the external indicator light on the environment. In other words, although it is necessary to make external indicator light 16 to be bright enough to be recognizable from a far off place, it may be bothering to the patient being treated (or other patients in the vicinity), so that it can contribute to the comfort of the patient if the light reduces its intensity when the operator approaches operation input unit 12.

In a case of a device wherein external indicator light 16 emits light when an abnormality occurs or a dialysis treatment is finished, this makes it possible for the operator such as a medical doctor to reduce the intensity by simply walking up to the front of operation input unit 12, making it labor saving compared to a case where the intensity has to be reduced by a manual operation. It can also be controlled in such a way as to turn off external indicator light 16 when the detection signal is received by control unit 19, which not only minimizes the effect of the lighting on the environment but also contributes to labor saving.

In the abovementioned constitution wherein external indicator light 16 is turned off or its intensity is reduced when control unit 19 receives the detection signal, the following effect can be achieved: In a typical dialysis treatment facility, where a plurality of dialysis devices arranged, the abovementioned constitution makes it possible for other operators such as medical doctors to see from a distance which of the external indicator lights 16 is turned off or reduced intensity thereof because it is attended by an operator, and allow them to decide which dialysis device they should go to.

The invention is not limited to the above embodiment, but rather it can be applied to other type of dialysis devices. In other words, the device according to the embodiment is a type wherein dialysate is supplied to the dialyzer while the dialysate of a specific concentration is produced from a condense dialysate in dialysis device main unit 1, the present invention can also be applied to a dialysis device wherein the dialysate of said specific concentration is prepared beforehand in a separate device and is supplied to the dialyzer. Moreover, the present invention can be applied to, in addition to the medical device of the embodiment where blood dialysis (HD) is applied, to all other kinds of blood purifying devices wherein blood is purified through extracorporeal circulation, such as, hemo filtration (HF), hemo dialyzing filtration (HDF), and plasma separating.

The invention is also applicable, in addition to blood purifying devices, to infusion devices comprising an operation input unit and an operation unit. Such an infusion device is for administering a drug into the patient's body and comprises an input detection means that detects the presence of the operator in the vicinity of the operation input unit as in the abovementioned embodiment and a control unit for controlling the operation unit to perform operations based on input through the operation input unit only when the operator is detected by the human body detection means, so that it can prevent the operation unit's operation when the operator is not present in the vicinity of the operation input unit and achieve both the ease of operation through the operation input unit and the patient's safety at the same time.

Of course, in addition to the blood purifying devices and infusion devices mentioned above, the invention can be applied to all kinds of medical devices that can adversely affect the patient's body if the operation unit operates based on an error signal from the operation input unit.

The Effects of the Invention

The invention according to claim 1 controls to allow input operations through the operation input unit for instructing the operation unit's operations or allow the operation unit to operate based on the input through the operation input unit only when the operator is detected by means of the human body detection means, so that the input operations to the operation unit or the operation unit's operations due to malfunctions or external noises when the operator is not present in the vicinity of the operation input unit can be prevented, thus achieving both the ease of operation through the operation input unit and the patient's safety at the same time.

The invention according to claim 2 makes it possible to cancel the control unit's controls, so that the operator can choose either to allow operations of the operation unit based on input information through the operation input unit only when the operator is detected by the human body detection means, or to allow operations of the operation unit based on input information through the operation input unit regardless of whether the operator is detected by the human body detection means or not, thus improving the ease of operation on the medical device.

The invention according to claim 3 provides a display means that displays specific information such as the operation unit's operation status, and said display means displays only when the operator is detected by the human body detection means, it makes it possible not only to achieve ease of operation and safety simultaneously, but also to minimize the power consumption of the display means, thus reducing the running cost of the medical device.

The invention according to claim 4 provides a display means comprising a liquid crystal display panel with a backlight, which turns on or increases its intensity to performs its specified display when the human body detection means detects the operator, so that it not only reduces the running cost of the medical device but also improves its ease of operation.

The invention according to claim 5 provides a sound output means that emits a specific sound depending on the operation status of the operation unit and the output of said sound output means is controlled by the detection of the operator by the human body detection means, so that it is not only capable of achieving ease of operation and safety simultaneously, but also minimizing the deterioration of the environment due to sound.

The invention according to claim 6 provides an external indicator light that turns on in accordance with the operation status of the operation unit and is capable of controlling the intensity of said external indicator light based on the detection of the operator by means of the human body detection means, so that it makes it possible to recognize various operation statuses of the operation unit or whether it is operated by the operator from a distance while minimizing the deterioration of the environment due to the illumination of the external indicator light.

The invention of claim 7 provides a human body detection means equipped with an illumination means that irradiates infrared light and a light receiving means for receiving its reflection for detecting the presence of the operator in the vicinity of the operation input unit, so that the detection of the operator can be performed always accurately.

| Description of keys used in the drawings | |
|---|---|
| 1 | Dialysis device main body |
| 2 | Dialyzer (blood purifier) |
| 3 | Blood circuit |
| 4 | Reciprocating pump |
| 5 | Heater |
| 6 | Deaeration pump |
| 7 | Deaeration chamber |
| 8, 9 | Suction pump |
| 10, 11 | Mixing chamber |
| 12 | Operation input unit |
| 12a | Liquid crystal panel (display means) |
| 12b | Cabinet |
| 13 | Syringe pump (operation unit) |
| 14 | Arm |
| 15 | Pole |
| 16 | External indicator light |
| 17 | Speaker (sound output means) |
| 18 | Human body detection means |
| 18a | Light emitting means |
| 18b | Light receiving means |
| 19 | Control unit |
| 20 | Air bubble detector (operation unit) |

What is claimed is:

1. A medical device comprising:
    an operation input unit configured for an operator to enter instructions;
    an operation unit configured to perform prescribed operations required for medical treatment based on input from said operation input unit;
    a human body detection unit configured to actively detect a presence of the operator in a vicinity of said operation input unit; and
    a control unit configured to provide a control function either to allow said operation input unit to instruct said operation unit to perform said prescribed operations, or to allow said operation unit to operate based on the input entered into said operation input unit, only when said human body detection unit is detecting the operator.

2. A medial device as claimed in claim 1, further comprising:
    a display configured to display specific information such as operating conditions of said operation unit, wherein said display executes a specific display when said human body detection unit detects the operator.

3. A medical device as claimed in claim 2, wherein
    said display comprises a liquid crystal display panel equipped with a backlight, and executes the specific display by either lighting said backlight or raising intensity of the backlight when said human body detection unit detects the operator.

4. A medical device as claimed in claim 1, wherein said control function provided by said control unit can be cancelled.

5. A medical device as claimed in claim 1, further comprising:
    a sound output unit configured to issue specific sounds in accordance with operation conditions of said operation unit, wherein an output by said sound output unit is controlled based on a detection of the presence of the operator by said human body detection unit.

6. A medical device as claimed in claim 1, further comprising:
    an external indicator light configured to illuminate in accordance with operation conditions of said operation unit, wherein
    luminescence intensity of said external indicator light is made controllable based on a detection of the operator by said human body detection unit.

7. A medical device as claimed in claim 1, wherein:
    said human body detection unit comprises an illumination unit configured to irradiate an infrared light and a light receiving unit configured to receive a reflection of the infrared light; and
    the presence of the operator in the vicinity of said operation input unit is detected as said light receiving unit receives the reflection.

8. A medial device as claimed in claim 7, further comprising:
    a display configured to display specific information such as operating conditions of said operation unit, wherein said display executes a specific display when said human body detection unit detects the operator.

9. A medical device as claimed in claim 7, further comprising:
    a sound output unit configured to issue specific sounds in accordance with operation conditions of said operation unit, wherein an output by said sound output unit is controlled based on a detection of the presence of the operator by said human body detection unit.

10. A medical device as claimed in claim 7, further comprising:
    an external indicator light configured to illuminate in accordance with operation conditions of said operation unit, wherein
    luminescence intensity of said external indicator light is made controllable based on a detection of the operator by said human body detection unit.

11. A medical device as claimed in claim 1, wherein said human body detection unit detects the presence of the operator without a physical contact between said human body detection unit and the operator.

12. A medical device as claimed in claim 11, further comprising:
   a sound output unit configured to issue specific sounds in accordance with operation conditions of said operation unit, wherein an output by said sound output unit is controlled based on a detection of the presence of the operator by said human body detection unit.

13. A medical device as claimed in claim 11, further comprising:
   an external indicator light configured to illuminate in accordance with operation conditions of said operation unit, wherein
   luminescence intensity of said external indicator light is made controllable based on a detection of the operator by said human body detection unit.

14. A medical device as claimed in claim 1, wherein said human body detection unit is at least one of an infrared detection device, a thermal detection device, and an image recognition device.

15. A medical device as claimed in claim 14, further comprising:
   a sound output unit configured to issue specific sounds in accordance with operation conditions of said operation unit, wherein an output by said sound output unit is controlled based on a detection of the presence of the operator by said human body detection unit.

16. A medical device as claimed in claim 14, further comprising:
   an external indicator light configured to illuminate in accordance with operation conditions of said operation unit, wherein
   luminescence intensity of said external indicator light is made controllable based on a detection of the operator by said human body detection unit.

* * * * *